(12) United States Patent  (10) Patent No.: US 8,570,521 B2
Chumachenko et al.  (45) Date of Patent: Oct. 29, 2013

(54) OPTICAL SYSTEM DESIGN FOR WIDE RANGE OPTICAL DENSITY MEASUREMENTS

(75) Inventors: Nataliya Chumachenko, Boulder, CO (US); Yehor Novikov, Boulder, CO (US)

(73) Assignee: Reach Devices, LLC, Boulder, CO (US)

( * ) Notice: Subject to any disclaimer, the term of this patent is extended or adjusted under 35 U.S.C. 154(b) by 369 days.

(21) Appl. No.: 12/951,044

(22) Filed: Nov. 21, 2010

(65) Prior Publication Data

US 2012/0127470 A1  May 24, 2012

(51) Int. Cl.
*G01N 21/00* (2006.01)

(52) U.S. Cl.
USPC .......................................................... 356/440

(58) Field of Classification Search
USPC ................... 356/335–343, 432–444
See application file for complete search history.

(56) References Cited

U.S. PATENT DOCUMENTS

| | | | | |
|---|---|---|---|---|
| 3,588,496 A * | 6/1971 | Snowman | ........................ | 250/343 |
| 3,726,598 A * | 4/1973 | Gilby et al. | ........................ | 356/244 |
| 4,011,451 A * | 3/1977 | Nelson | ........................ | 250/343 |
| 4,066,362 A * | 1/1978 | Carter | ........................ | 356/409 |
| 4,286,881 A * | 9/1981 | Janzen | ........................ | 356/440 |
| 4,501,969 A * | 2/1985 | Lymneos | ........................ | 250/373 |
| 4,795,262 A * | 1/1989 | Morris et al. | ........................ | 356/436 |
| 4,844,611 A * | 7/1989 | Imahashi et al. | ........................ | 356/246 |
| 5,214,593 A * | 5/1993 | Magnussen et al. | ........................ | 702/32 |
| 5,290,520 A * | 3/1994 | Maystre et al. | ........................ | 422/82.05 |
| 5,459,566 A * | 10/1995 | Pearson et al. | ........................ | 356/246 |
| 5,602,647 A * | 2/1997 | Xu et al. | ........................ | 356/435 |
| 5,815,258 A * | 9/1998 | Nakanishi | ........................ | 356/246 |
| 6,124,937 A * | 9/2000 | Mittenzwey et al. | ........................ | 356/432 |
| 6,188,474 B1 * | 2/2001 | Dussault et al. | ........................ | 356/246 |
| 6,342,948 B1 * | 1/2002 | Gilby | ........................ | 356/436 |
| 6,628,382 B2 * | 9/2003 | Robertson | ........................ | 356/246 |
| 6,747,740 B1 * | 6/2004 | Leveille et al. | ........................ | 356/446 |
| 6,867,861 B2 * | 3/2005 | Martino et al. | ........................ | 356/319 |
| 7,369,226 B1 * | 5/2008 | Hewitt | ........................ | 356/244 |
| 7,777,887 B2 * | 8/2010 | Pralle et al. | ........................ | 356/440 |
| 7,800,751 B1 * | 9/2010 | Silver et al. | ........................ | 356/246 |
| 7,808,641 B2 * | 10/2010 | Salerno et al. | ........................ | 356/440 |
| 7,847,944 B2 * | 12/2010 | Buettner et al. | ........................ | 356/436 |
| 7,936,463 B2 * | 5/2011 | Kiesel et al. | ........................ | 356/519 |
| 2002/0080349 A1 * | 6/2002 | Armstrong et al. | ........................ | 356/246 |
| 2008/0079942 A1 * | 4/2008 | Buettner et al. | ........................ | 356/436 |
| 2008/0221711 A1 * | 9/2008 | Trainer | ........................ | 700/54 |

FOREIGN PATENT DOCUMENTS

| | | | | | |
|---|---|---|---|---|---|
| JP | 07321005 A | * | 12/1995 | ............ | G02B 27/18 |
| JP | 2007271365 A | * | 10/2007 | ............ | G01N 21/03 |

OTHER PUBLICATIONS

Hiroshi et al, Machine Translation of JP2007271365A, Apr. 13, 2013, GoogleTranslate function, pp. 1-15.*
Hirschfeld, Dynamic Range improvement in Fourier Transform Infrared Spectrometry, Analytical Chemistry, vol. 50, No. 8, Jul. 1978, pp. 1225-1226.*
Dasgupta, Multipath Celles for Extending Dynamic Range of Optical Absorbance Measurements, Analytical Chemistry, vol. 56 No. 8, Jul. 1984, pp. 1401-1403.*

* cited by examiner

*Primary Examiner* — Gregory J Toatley
*Assistant Examiner* — Shawn Decenzo

(57) ABSTRACT

This invention relates to optical cell geometry and to the arrangement of optical elements in an absorbance (at 200 nm to 50000 nm) detector. The invention allows to significantly expand the dynamic range of an optical density measuring instrument without affecting the signal to noise ratio. The invention also allows to enhance the precision of said instrument by eliminating the artifacts that arise from partial reflections of the incident beam, which occur on the passage of the beam through interfaces between different media.

1 Claim, 5 Drawing Sheets

OPTICAL SYSTEM DESIGN FOR WIDE RANGE OPTICAL DENSITY MEASUREMENTS

BACKGROUND OF THE INVENTION

1. Field of the Invention

The present invention relates to optical density measuring instruments, including chromatography detectors that measure the concentration of a substance in a solution or a gas phase.

2. Background Art

The flourish and proliferation of biotechnology and drug discovery in the modern age would have been impossible without the concurrent intensive research in the field of organic chemistry. On average, a researcher in an organic chemistry laboratory performs at minimum one preparative flash column chromatography separation daily. For the reasons explained below, contemporary optical detectors are unsuitable and impractical for real-time visualization of the predominant number of these separations, and researchers are often limited to old, laborious and time consuming TLC (thin layer chromatography) visualization methods. While the invention disclosed here is designed to be employed as a part of virtually any optical detector, the invention is paramount for continuous flow liquid chromatography optical detectors, as it finally makes the use of such detectors realistic for conducting routine, frequent preparative flash chromatography experiments.

Additionally, the invention will facilitate real-time analysis of blood, dye and other samples of high molecular absorbtivity; improve the separations/analysis in biotechnology, pharmaceutical, fermentation and/or other sectors of industry and/or research fields.

In general, an optical detector includes at minimum: a light source (200 nm to 50000 nm), an optical system used for collection and redirection, a sample cell that contains a solution of a sample to be measured, and a photometer. The optical system directs a beam of incident light of known intensity from the light source onto a sample cell, and also directs the light transmitted through the sample cell onto the photometer.

If no losses of light occurred during the measurements, the amount of light absorbed by the sample would be equal to the difference between the amount of incident light directed onto the sample cell and the amount of light transmitted through the sample cell. The accurate value of the absorbance (A, measured in Absorption Units, AU) of the sample would then be found as:

$$A = -\log(\text{Intensity of light emerging from the sample cell/Intensity of light directed onto the sample cell})$$

where $\log(x)$ is the base-ten logarithm of x.

Practically, this means that that a contemporary detector can not reliably measure absorbance exceeding 4 AU:

for A=1.00: 90% of the photons are absorbed, 10% reach the detector;

for A=2.00: 99% of the photons are absorbed, 1% reach the detector;

for A=3.00: 99.9% of the photons are absorbed, 0.1% reach the detector;

for A=4.00: 99.99% of the photons are absorbed, 0.01% reach the detector.

On the other hand, according to Beer-Lambert law: $A = E \cdot b \cdot C$, where:

A is the measured absorbance of a sample, expressed in Absorption Units, AU;

E is molar absorption coefficient (at a particular wavelength $\lambda$) of the compound that is analyzed, expressed in L/(mol*cm);

b is optical path length, which is equal to the distance between the inner edges of the sample cell, expressed in cm;

C is the concentration of the compound in solution, expressed in mol/L.

On a routine preparative purification by flash chromatography of 100 mg of a target compound, for example benzoic acid, using 10 g of silica, the appropriate amount of solvent would be around 100 mL. In case of a successful separation, the volume of the fraction containing the benzoic acid would be no more than 10 mL, which corresponds to the concentration of benzoic acid in the detector's flow cell being at least 100 mg/10 mL=10 g/L. Given that the formula weight of the benzoic acid is 136.15 g/mol the concentration of benzoic acid in the detector's flow cell will be at least 10/136.15=0.073 mol/L.

Molar absorption coefficient of the benzoic acid is E=14400 L/(mol cm) at $\lambda$=242 nm.

Thus, according to the Beer-Lambert law:

$$A = E \cdot b \cdot C = 14400 \cdot b \cdot 0.073 = 1050 \cdot b$$

for the width of the sample cell b=1 cm, the absorption will reach A=1050 AU;

for the width of the sample cell b=1 mm, the absorption will reach A=105 AU;

for the width of the sample cell b=0.1 mm, the absorption will reach A=11 AU;

for the width of the sample cell b=0.01 mm, the absorption will reach A=1.1 AU.

Thus only 0.01 mm path length cell could be used for the detection in this case. On the other side, if there is about 1% of benzyl alcohol (E=12 L/(mol cm) at $\lambda$=250 nm) present as an admixture in the benzoic acid, the same calculations would yield only A=0.000011 AU optical density value. This value is well below the typical baseline drift of all commercial detectors. To reliably detect the benzyl alcohol one needs to use at least 1 mm path length cell, which would give 0.0011 AU reading easily observable by most detectors.

It is important to note that the differences in extinction coefficients and concentrations of the components of a mixture to be separated are often even more pronounced. This example illustrates that a routine preparative separation in an organic chemistry laboratory requires the detector to simultaneously collect the readings for multiple path lengths.

The need for multi-path length flow cells has been widely recognized in the art and has been addressed by two approaches. In general, these two approaches use a total of three types of design of such flow cells have been proposed.

The first approach utilizes two different designs of static flow cells of calculated geometries that simultaneously allow the incident light to pass through different pass lengths through the sample.

Design 1 includes "ladder-type" cells, which allow for at least two or more different optical path lengths. The design is proposed, for example, in U.S. Pat. No. 6,342,948 (Gilby) and U.S. Pat. No. 5,214,593 (Magnussen et al.). A method of correcting absorbance measuring for such cells is disclosed in Patent application publication US2008/0079942 A1 (Buettner, W; Kuderer, W.). The ladder-type cells are also discussed in the articles: Hirschfeld, T. Analytical Chemistry, 1978, Volume 50, pages 1225-1226; Dasgupta, P. K. Analytical Chemistry, 1984, Volume 56, page 1401-1403.

However, a number of problems, in part described below, are inherent to such "ladder-type" cells. Regardless of the geometry of a thin part of a "ladder cell" cell, high hydrodynamic resistance leads to very low flow rates through this part. To achieve reasonable flow rates, the cell must contain a bypass channel. Thus the flow rate will inevitably be slower in the thinner (for example 0.01 mm) part of the ladder cell, than in the rest of the cell, the thicker part(s) serving as bypass channel(s). A part of the sample will inevitably become trapped in the thinner region of the cell and will only slowly exchange with the main stream of the sample. This phenomenon leads to delayed readings and artificially broadened peaks. The effect becomes even more profound for higher-viscosity solvents routinely used in biochemical separations, for example water and n-butanol. Moreover, for thin cells with parallel optical windows, light interference becomes a serious problem. For example, a 0.01 mm path length corresponds to only 40 wavelengths of the 250 nm light. The amount of interference is dependent on the refractive index of the sample, thus introducing artifacts that vary and can not be accounted for in the responses of the detectors. Additionally, the maintenance of such cells is troublesome, since the thinner part has a tendency to get pemanetly clogged.

Design 2 described in the U.S. Pat. No. 5,602,647 (Xu, at al.) involves a flow cell that has a triangular shape in its cross-section. Such design eliminates the problems of high hydrodynamic resistance and interference inherent to design 1 ("ladder-type" cell). However, these advantages are negated by the fact that only a very small fraction of light travels through the sufficiently short path lengths for measurements of concentrated samples. As a result, the concentration range that can be measured using triangular cells is much less than for "ladder cells."

The second approach utilizes a design of dynamic flow cells of variable, adjustable widths.

Design 3 could be generalized as the cells with mechanically adjusted optical path length, which can be accomplished either manually of automatically by the spectrometer software. However, the relates to the invention described here only tangentially, as it takes the absorbance reading at a single path length, which is adjusted afterwards. This design, described, for example, in U.S. Pat. No. 7,808,641 (Salerno et al.), U.S. Pat. No. 7,369,226 (Hewitt), U.S. Pat. No. 6,188,474 (Dussault et al.), U.S. Pat. No. 6,628,382 (Robertson), U.S. Pat. No. 6,747,740 (Leveille et al.) U.S. Pat. No. 6,867,861 (Martino, et al.), U.S. Pat. No. 4,286,881 (Janzen), U.S. Pat. No. 4,066,362 (Carter), U.S. Pat. No. 3,726,598 (Gilby et al).

For the invention described here, it should also be noted that a broad family of patents, for example: U.S. Pat. No. 7,777,887 (Pralle, et al.), U.S. Pat. No. 5,815,258 (Nakanishi), U.S. Pat. No. 5,459,566 (Pearson, et al.) employs non-flat cell surfaces to collect/focus the light beam(s). However, the inventions disclosed in all of these patents are designed to have/maintain a constant path length of the light traveling through the sample, and the non-flat surface is primarily utilized to focus/collect/redirect beam(s) of electromagnetic radiation.

For the sake of simplicity, the previous discussion ignores the fact that, in reality, two kinds of light losses inevitably occur during optical density measurement: absorption losses and reflection losses. Absorption losses occur due to the absorption of light by the solvent used to dissolve the sample and by the material of the sample cell windows. Absorption losses are usually negligible. Reflection losses occur due to partial reflection of the incident light off the interfaces between different transparent media used within a spectrophotometer. Reflection losses of light are more severe and are discussed below in more detail.

According to the natural law of refraction described by the Fresnel equations, when light travels through an interface between two media of different refractive indexes, both reflection and refraction of light may occur.

On passage through an optical cell, a beam of light inevitably encounters at least four interfaces of different media: detector interior/cell material, cell material/sample solution, sample solution/cell material, and cell material/detector interior. For example, it can be air/quartz, quartz/solvent, solvent/quartz and quartz/air interfaces. The fractions of light lost on reflection from the interfaces between detector's interior/cell's material and cell's material/detector's interior are constant for a given detector at a given temperature and atmospheric pressure, and can be measured once per experiment, and then used for the correction of the output value by detector's software. However, the fractions of light lost on reflections from the interfaces between cell material/sample media and sample media/cell material varies depending on the refraction index of sample solution. To achieve reproducible readings, these losses have to be measured for each particular sample media, and then compensated for. To do so, a reference cell is used.

The reference cell is physically identical to the sample cell and contains pure solvent identical to that in the sample cell. The incident beams of equal intensity are passed through both cells and the value of the absorbance (A) of the sample is found as:

$$A = -\log(\text{Intensity of the light transmitted through the sample cell/Intensity of the light transmitted through reference cell})$$

where log(x) is the base-ten logarithm of x.

However, the use of a reference cell is impractical for gradient elution of samples. The composition of the solvent is changing with time and so does the refractive index, which, in turn, affects the measured optical density value. Also, it was found that when a refractive index gradient is encountered within the flow cell, so-called dynamic fluid lenses form, which create a problem that seriously impacts the reliability of the readings of the detector.

To circumvent the problem of a varying refractive index, a conical (tapered) flow-cell, where light enters at the narrow end of the cell, and a photometer is situated at the wider end of the cell, was proposed in U.S. Pat. No. 4,501,969 (Lymneos) and U.S. Pat. No. 4,011,451 (Nelson). Later, it was found that a large inclination of the inner wall is necessary to efficiently suppress the lens effect that otherwise distorts light passing through the cell. It was then emphasized that such an inclination consequently increases the flow cell volume beyond the practical limit. Thus, a variation of a split-type cell, altered to have a reduced volume has been proposed U.S. Pat. No. 4,844,611 (Imahashi at al.). However, a conical flow cell does not allow to compensate for the light reflected off the cell window(s).

Another approach was disclosed in U.S. Pat. No. 4,795,262 (Morris et al.). A retroreflective array was placed in the path of light exiting the sample cell, which caused the light beams to reverse and to pass back through the sample cell closely along their original paths thus undoing the original distortions. The reversed beam of light was then directed to a photometer for the quantification. The approach has two serious drawbacks. Firstly, the variable amount of light that was reflected from the entrance cell window boundaries is directed to the photometer even before reaching the sample. Secondly, at least a half of the light that has passed thought the sample is lost on the beam splitter while being diverted to the photometer, which significantly decreases signal to noise ratio.

A combined approach to simultaneously measure the optical density, dispersion, refraction and fluorescence was proposed in U.S. Pat. No. 6,124,937 (Mittenzwey et al.) The approach is based on a multiple reflection cavity with one semitransparent window where light travels along a fairly long path through the sample. The reflected and diffused light is collected from the side of the cavity facing the light source by using fiber optics, while light emerging from the other side of the cavity is quantified to calculate the absorption of the sample. However, the proposed design is extremely complex and ineffective, and precludes usage of the multi-path length cells.

Yet another approach included continuous automatic addition of a refractive index equalizing reagent into the mixture U.S. Pat. No. 5,290,520 (Maystre et al.), however such approach is impractical and the equalizing reagent will severely and often irreversibly contaminate the mixture that is analyzed.

BRIEF SUMMARY OF THE INVENTION

The present invention provides a multi-path length optical cell, wherein light from different sample path lengths is combined and is quantified by the same photometer.

The cell is comprised of an entrance optical window and an exit optical window, where at least one of these windows includes a non-flat surface in immediate contact with the sample. That non-flat curvature of the said surface alters the path length of a beam of electromagnetic radiation through a sample depending on the position on the surface.

The rays that travel through the part of the sample that is confined by the non-flat area of the internal surface in contact with the media, fall onto different spots of this surface. Since different cross-sections of the surface are at non-equal distances from the opposite window's internal surface, different rays must travel different distances through the sample.

The artifacts that arise from the partial (specular) reflections of the incident beam, which occur on the passage of the beam through interfaces between different media, are eliminated by implementing the following design: the incident beam of light falls onto a beam-splitter, and the major part of the beam travels through the beam splitter, passes through an optical cell, and finally reaches the first photometer. The parts of the incident beam that are reflected in the direction of the light source travel back to the said beam splitter. The beam splitter redirects a known portion of this reflected light toward the second photometer. The readings of the second photometer serve two purposes. Firstly, they allow to correct the readings of the first photometer for calculation of the sample's absorption. Secondly, they allow for measurement of the refractive index of sample.

DETAILED DESCRIPTION OF THE PREFERRED EMBODIMENTS

An embodiment of the present invention is now described with reference to the accompanying drawings.

Figure 1:
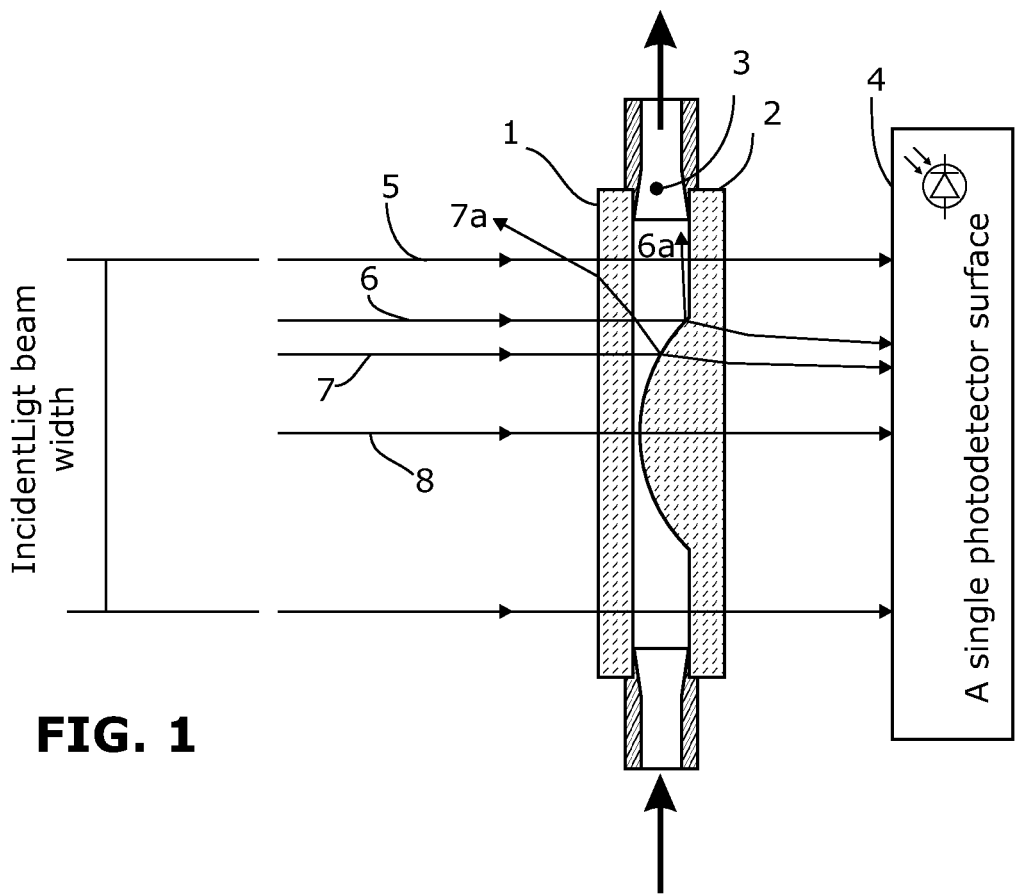
FIG. 1 is a cross-section of the drawing of the optical cell according to the claim 1.

FIG. 1 shows embodiment 1 of the flow cell for optically measuring the absorption of electromagnetic radiation, such as UV light, visible light or infrared light, according to the first claim of the present invention. The cell is comprised of an entrance optical window 1, and an exit optical window 2, while media to be analyzed 3 is placed between said windows. Both window 1 and window 2 are transparent to the incident electromagnetic radiation to be measured. The shape of window 1 is that of a sheet of transparent material, comprised of two flat, parallel surfaces: the external surface that faces the incident light, and the internal surface that is in contact with the sample media 3. The structure of window 2 includes two pseudo-parallel surfaces: the surface in contact with the sample (internal surface) and the external surface. The internal surface always has a non-flat convex curvature that extends into the media, and, preferably but not necessarily, consists of a segment of a sphere on a flat surface. The opposite (external) surface of window 2 is flat.

A beam of electromagnetic radiation, for example a beam of UV light, visible light or infrared light, is directed onto the entrance window 1, the beam oriented perpendicularly (at 90 degrees angle) to the window's external surface. The cross-section of the beam of light is as least so large as to cover the entrance window 1. The beam consequently travels through the entrance window 1, then through the sample 3, then the exit window 2, and finally reaches the photometer 4 to be quantified. In this specific embodiment, photometer 4 has a sensitive area large enough to intercept and detect all rays that are coming out of exit window 2.

Referring again to FIG. 1, several rays of the incident beam are illustrated and numbered 5 through 8, each ray traveling a different distances through the sample. Ray 5 travels through the sample via the maximum available path length of the flow cell, the path length being defined by the distance between the internal surface of window 1 and the flat portion of the internal surface of window 2. The rays 6 and 7 travel through the part of the sample which is confined by the convex area of the exit widow 2. Ray 6 falls onto the spot of the convex surface of window 2 that is situated towards the periphery, while ray 7 falls onto the spot of the convex surface of the window 2 that is situated towards the center. Therefore, since the periphery of the convex internal surface of window 2 is at a greater distance from the internal surface of window 1 than the central part of the convex surface, rays 6 and 7 travel different distances through the sample 3, ray 6 traveling a longer distance than ray 7. Ray 8 travels the shortest path length through the sample, which is only a few wavelengths long. Also, in embodiment 1, the convex surface of exit window 2 is designed to direct rays 6a and 7a—the components of rays 6 and 7 reflected by this surface—away from photometer 4.

Figure 2:
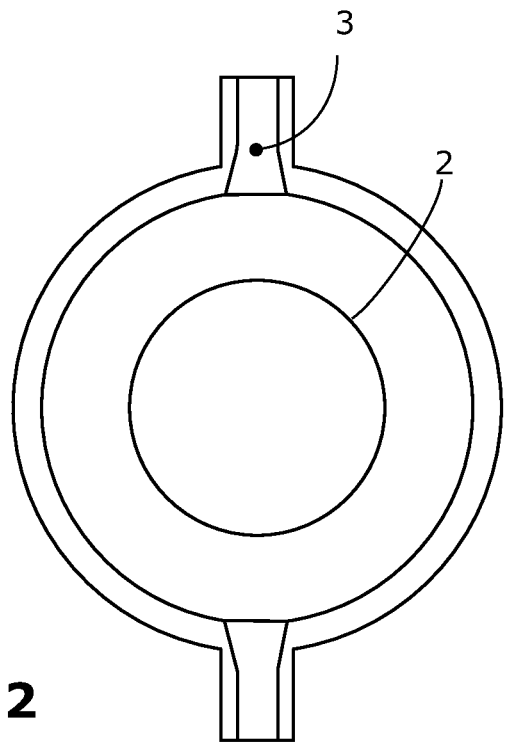
FIG. 2 is a top view of the said cell.

FIG. 2 presents the results of ray-tracing calculations, which were performed to demonstrate the superiority of the flow cell described here as embodiment 1 of claim 1, over the flow cell designs previously known in the art, which are described in the "Background Art" section of this document. Three optical cells were compared: an example of the "ladder-type" cell 9, an example of the triangular-type cell 10, and cell 11 that serves as an embodiment 1 of claim 1 of this document. FIG. 2 shows the cross-sections of each of the three cells 9, 10, and 11. The smallest distance between the inner surfaces of the optical windows in each cell is 0.01 mm, except cell 11, where the distance is 0.001 mm. The largest distance between the inner surfaces of the windows in each cell is 1 mm.

The calculations were conducted for the example of benzoic acid that was described in the "Background Art" section, which has molar absorption coefficient E=14400 L/(mol cm) at λ=242 nm.

In FIG. 2, the vertical (Y) axis designates the percentage of the light reaching the photometer after traveling through the sample of benzoic acid contained in the cells 9, or 10 or 11. The horizontal (X) axis in FIG. 2 designates the concentration of benzoic acid in the sample, in mol/L.

The amount of light reaching the photometer decreases with increasing concentration of benzoic acid in the sample. In the cases of cells 9 and 10, this decrease is dramatically faster than for the cell 11. Thus, cell 11 allows for a much broader range of sample concentration to be reliably analyzed.

The graphs in FIG. 2 also can be viewed as linearization functions that allow for the calculation the true value of the absorption of the sample from the measured amount of light. The linearization function for cell 11 does not have a true flexing point which is present in the linearization function for cell 9 or 10. A flexing point is a fragment of the linearization curve where two relatively linear portions of the curve with different slopes meet, causing the second derivative of the curve to momentarily but dramatically spike. Therefore, the concentration measurement accomplished close to the flexing point are prone to very large errors, since the slope of the curve is rapidly changing in that segment. Meanwhile, for cell 11, where the curve is relatively non-linear and smooth, a flexing point is nearly absent, creating for a very stable second derivative function with no observable spikes. The positions of the flexing points depend on the slight changes in cell geometry, the wavelength of the absorbed light, the flow rate, and other variable factors. Thus, the uncertainty of the measured absorption for cells 9 or 10 is not uniform, and cannot be easily estimated. The absence of such problems for cell 11 is truly advantageous.

Figure 3:
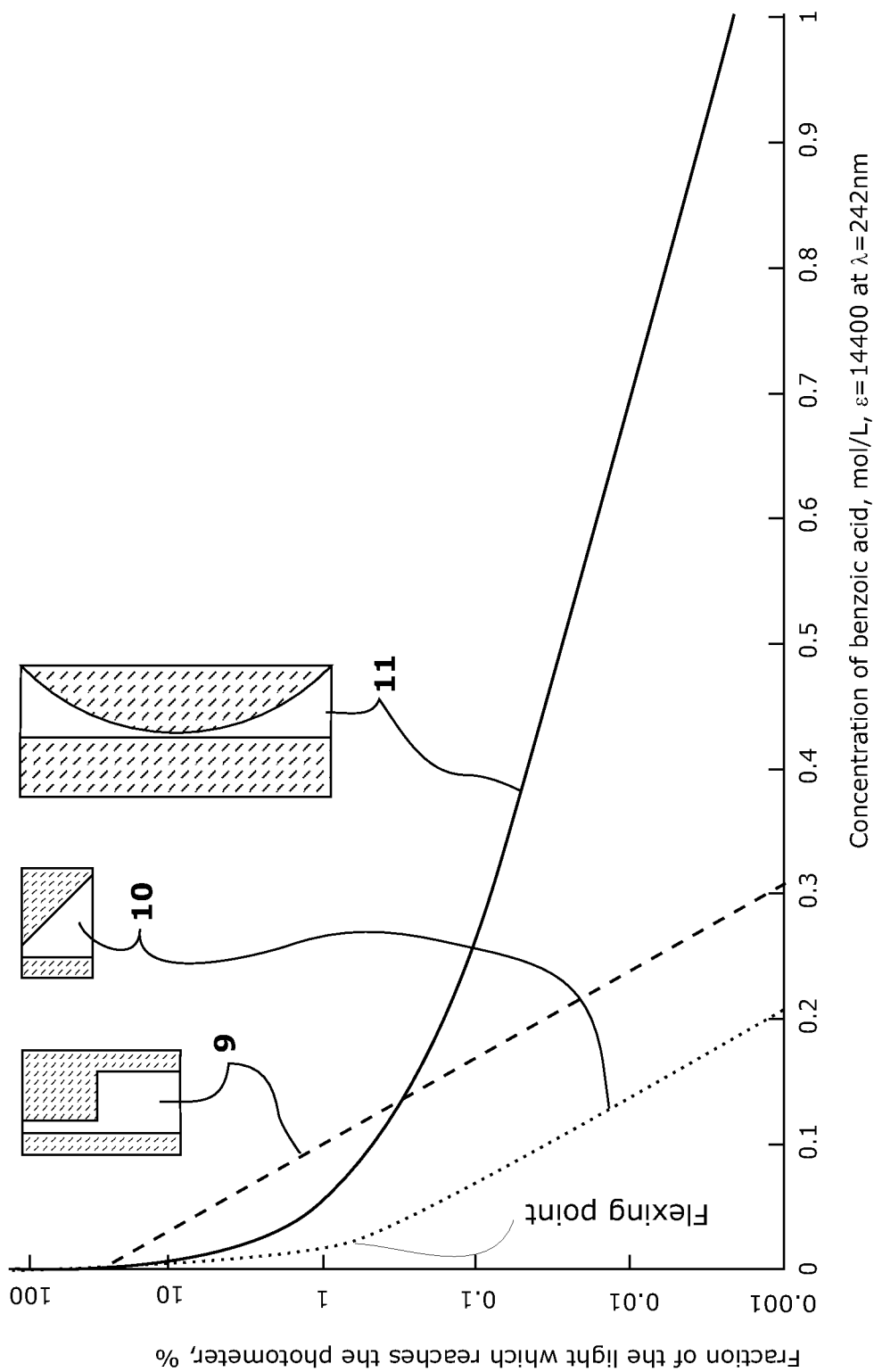
FIG. 3 presents the results of ray-tracing calculations of the optical cell according to claim 1.

FIG. 3 shows embodiment 2 of the optical density measuring instrument, according to the second claim of the present invention. In embodiment 2, light source 12 produces a beam of narrow bandwidth electromagnetic radiation, for example a beam of UV light, visible light or infrared light. The said beam falls onto beam splitter 13, and the major part of the beam (typically around 70%) travels through beam splitter 13, passes through flow cell 14, and finally reaches photometer 15. In embodiment 2, flow cell 14 has the conventional design comprised of two identical flat quartz optical windows 16a and 16b that confine the sample 17 to be analyzed.

As was described in "Background Art" section of this document, when passing through optical cell 14, the incident beam of light encounters four interfaces of different media: ambient air/quarts window 16a, quartz window 16a/sample 17, sample 17/quarts window 16b, and quarts window 16b/ambient air. According to the natural law of refraction, parts of the incident beam are reflected in the direction of light source 12 from each of the said interfaces. The reflected beams falls onto beam splitter 13, where always about 30% of the said beams are reflected toward photometer 18. The readings of photometer 18 serve two purposes. Firstly, they allow to correct the reading of photometer 15 for the subsequent calculation of the sample's absorption. Secondly, they allow for the measurements of the refractive index of sample 17.

Figure 4:
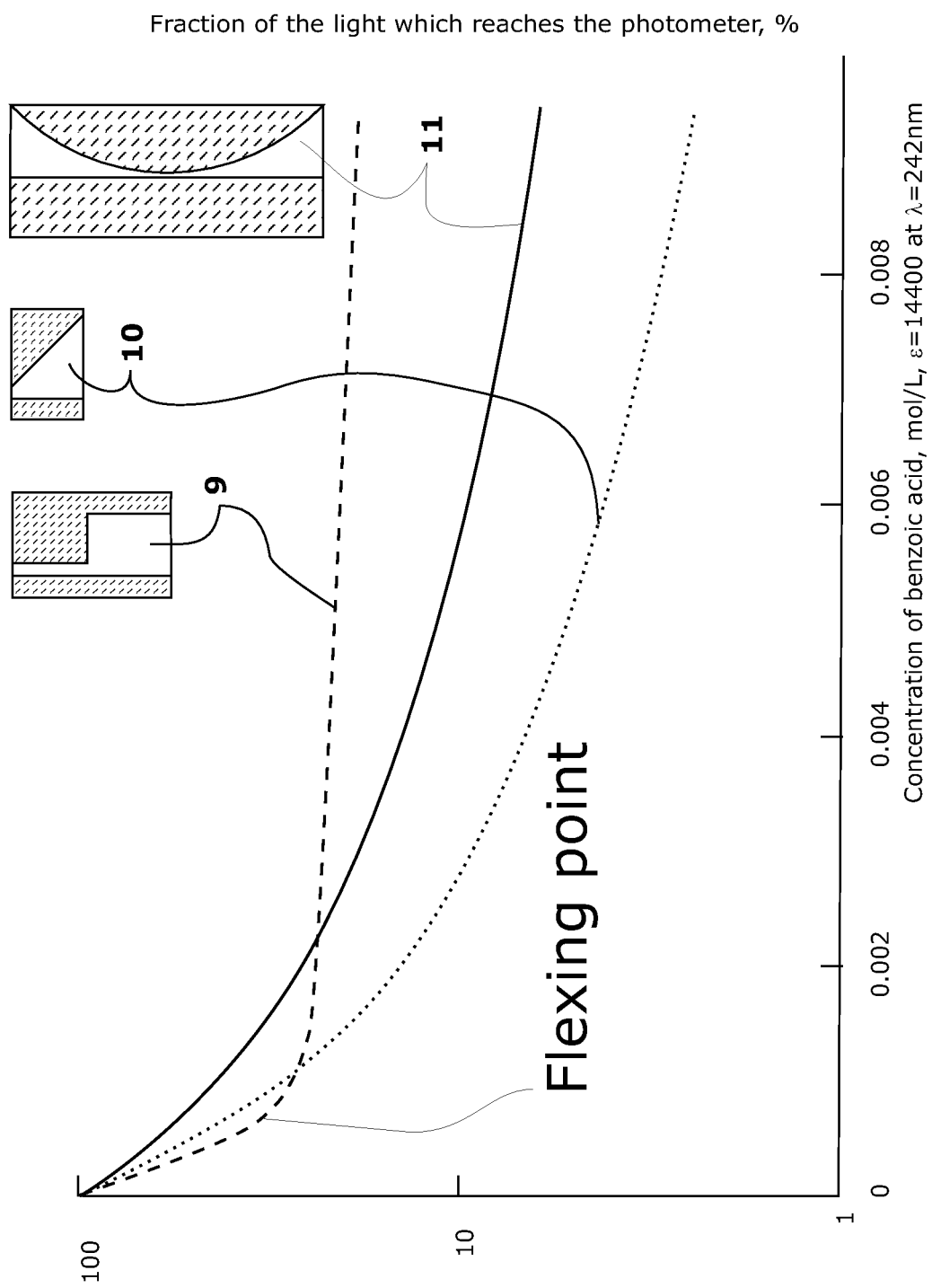
FIG. 4 is an expansion of the graph, presented on FIG. 3.
Figure 5:
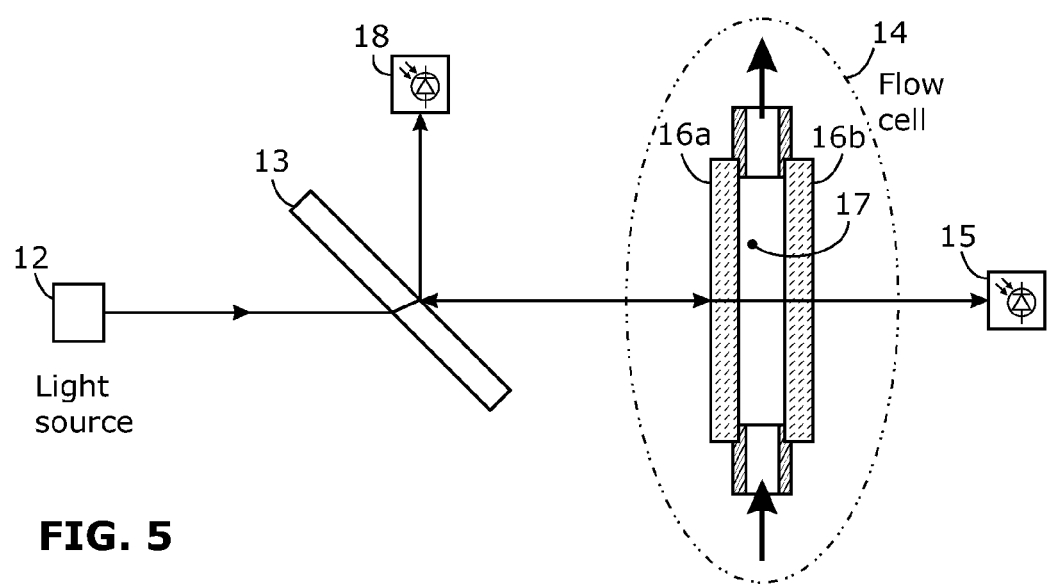
FIG. 5 shows embodiment 2 of the optical density measuring instrument, according to the claim 2.
Figure 6:
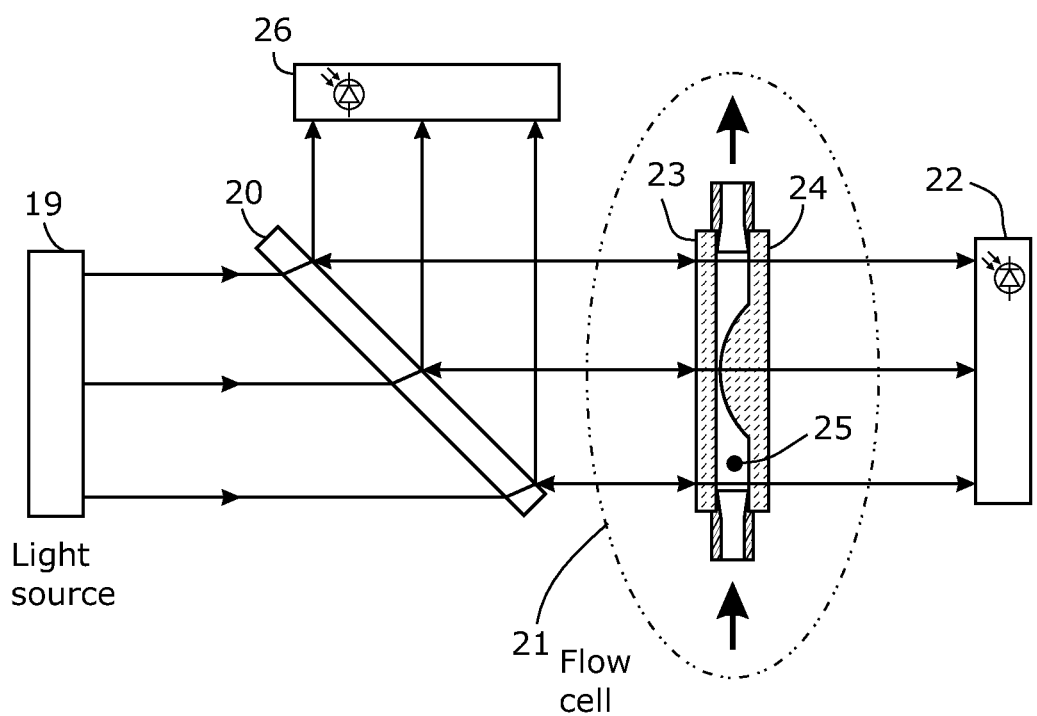
FIG. 6 shows embodiment 3 of the optical density measuring instrument, according to the first and second claim of the present invention

FIG. 4 shows embodiment 3 of the optical density measuring instrument, according to the first and the second claims of the present invention.

In embodiment 3, light source 19 produces a beam of narrow bandwidth electromagnetic radiation, for example a beam of UV light, visible light or infrared light. The said beam falls onto beam splitter 20, the major part of the beam (typically around 70%) travels through beam splitter 20, passes through flow cell 21, and finally reaches photometer 22. In embodiment 3, flow cell 21 has a design according to claim 1 and is comprised of flat entrance optical window 23, and exit optical window 24 that has a non-flat, convex part of the internal surface extending into the media to be analyzed 25.

On a passage through optical cell 21 the incident beam of light encounters four interfaces of different media: ambient air/quartz window 23, quartz window 23/sample 25, sample 25/quartz window 24, and quartz window 24/ambient air. According to the natural law of refraction, the parts of incident beam reflected from all phase interfaces, except for the non-parallel to window 23 part of the interface between sample 25/quartz window 24 will be directed back toward light source 19. The reflected beams will fall onto beam splitter 20, where about 30% of the said beams are reflected toward photometer 26. The final values of the optical density of the sample are calculated from the readings of photometers 22 and 26. The calculations are accomplished in real time by using a two-dimensional calibration function embedded into instrument's software.

What is claimed is:

1. An optical cell for optical density measurements at 200 nm to 50000 nm of solutions of radiation-absorbing samples comprising:
   a flat entrance optical window and a non-flat exit optical window in direct contact with the sample;
   wherein the windows are made of material(s) transparent to the electromagnetic radiation that is used to measure optical density of a sample;
   wherein the non-flat exit optical window is convex on the side of the non-flat exit optical window in direct contact with the sample;
   wherein the non-flat exit optical window is configured to create multiple, continuous, unequal path lengths for a beam of electromagnetic radiation passing through the sample.

* * * * *